US006972177B1

(12) United States Patent  (10) Patent No.: US 6,972,177 B1
Schreuder et al.  (45) Date of Patent: Dec. 6, 2005

(54) METHOD FOR THE DETECTION OF PRION DISEASES

(75) Inventors: Bram Edward Cornelis Schreuder, Lelystad (NL); Lucius Johannes Mattheus Van Keulen, Bunnik (NL); Maria Elisabeth Wilhelmina Vromans, Lelystad (NL); Johannes Pieter Maria Langeveld, Harderwijk (NL); Marinus Adrianus Smits, Harderwijk (NL)

(73) Assignee: Stichting Instituut voor Dierhouderij en Diergezondheid, Lelystad (NL)

( * ) Notice: Subject to any disclaimer, the term of this patent is extended or adjusted under 35 U.S.C. 154(b) by 0 days.

(21) Appl. No.: 09/155,794

(22) PCT Filed: Apr. 2, 1997

(86) PCT No.: PCT/NL97/00166

§ 371 (c)(1),
(2), (4) Date: May 20, 1999

(87) PCT Pub. No.: WO97/37227

PCT Pub. Date: Oct. 9, 1997

(30) Foreign Application Priority Data

Apr. 3, 1996 (EP) .......................................... 96200917

(51) Int. Cl.⁷ ......................... G01N 33/53; G01N 1/30; A61K 49/00
(52) U.S. Cl. ...................... 435/7.1; 424/9.1; 424/130.1; 424/139.1; 424/184.1; 435/40.5; 530/387.1
(58) Field of Search .............................. 424/9.1, 130.1, 424/139.1, 184.1; 435/7.1, 40.5; 530/387.1

(56) References Cited

U.S. PATENT DOCUMENTS

| 4,806,627 A | 2/1989 | Wisniewski et al. ........ 530/38.7 |
| 5,846,533 A | * 12/1998 | Prusiner et al. .......... 424/130.1 |
| 6,150,172 A | 11/2000 | Schmerr et al. |

FOREIGN PATENT DOCUMENTS

| WO | WO 93/23432 | 11/1993 | ........... C07K/13/00 |
| WO | WO 99/19360 | 4/1999 | |

OTHER PUBLICATIONS

Belt et al., Identification of the five allelic variants of the sheep PrP gene and their association with natural scrapie, Journal of General Virology, 1995, pp. 1–10.
Brown, Can Creutzfeldt–Jakob disease be transmitted by transfusion? 1995, pp. 472–477, Rapid Science Publishers.
Diringer et al., Scrapie infectivity, fibrils and low molecular weight protein, Nature, Dec. 1983, 476–78, Macmillan Journals Ltd.
Fraser et al., Transmission of bovine spongiform encephalopathy to mice, Journal of Small Animal Practice, 1988, p. 565, vol. 29.

Fraser, Murine Scrapie Strains, BSE Models and Genetics, Sub–acute Spongiform Encephalopathies, pp. 131–136, the Netherlands.
Fraser et al., Studies of the Lymphoreticular System in the Pathogenesis of Scrapie: The Role of Spleen and Thymus, J. Comp. Path., 1978, pp. 563–573, vol. 88.
Hilmert et al., A rapid and efficient method to enrich SAF–protein from scrapie brains of hamsters, Bioscience Reports, 1984, pp. 165–170, vol. 4.
Hadlow et al., Natural Infection of Suffolk Sheep with Scrapie Virus, The Journal of Infectious Diseases, Nov. 1982, pp. 657–664.
Henri et al., Recherche d'un temoin biochimique urinaire de l'infection du mouton par la tremblante, Bulletin de L'academie Veterinaire de France, pp. 139–145.
Meiner et al., Presence of prion protein in peripheral tissues of Libyan Jews with Creutzfeldt–Jakob disease, Neurology, Jul. 1992, pp. 1355–1360, vol. 42.
Mohri et al., Immunodetection of a disease specific PfP fraction in scrapie–affected sheep and BSE–affected cattle, Veterinary Record, 1992, pp. 537–539, vol. 131.
Muramoto et al., Accumulation of Abnormal Prion Protein in Mice Infected with Creutzfeldt–Jakob Disease via Intraperitoneal Route: A Sequential Study, American Journal of Pathology, Nov. 1993, pp. 1470–1479, vol. 143, No. 5.
Schreuder, Animal Spongiform Encephalopathies—An Update, Part I. Scrapie and Lesser Known Animal Spongiform Encephalopathies, Veterinary Quarterly, Oct. 1994, pp. 174–181, vol. 16, No. 3.
Schreuder, Animal Spongiform Encephalopathies—An Update, Part II. Bovine Spongiform Encephalopathy (BSE), Veterinary Quarterly, Oct. 1994, pp. 182–192, vol. 16, No. 3.
Van Keulen et al., Immunohistochemical Detection and Localization of Prion Protein in Brain Tissue of Sheep with Natural Scrapie, Vet Pathol, 1995, pp. 299–308, vol. 32.
Schreuder, et al., "Tonsillar biopsy and $PrP^{Sc}$ detection in the pre–clinical diagnosis of scrapie," *Papers and Articles*, pp. 1–9, Apr. 15, 1998.
Hadlow, et al., "Virologic and Neurohistologic Findings in Dairy Goats Affected with Natural Scrapie," *Vet. Pathol.* 17, pp. 187–199, 1980.
Doi, et al., "Western Blot Detection of Scrapie–associated Fibril Protein in Tissues outside the Central Nervous System from Preclinical Scrapie–infected Mice," *J. gen. Virol*, 69, pp. 955–960, 1988.

(Continued)

*Primary Examiner*—Rodney P Swartz
(74) *Attorney, Agent, or Firm*—TraskBritt (57) ABSTRACT

The invention provides methods for the detection of prion diseases, such as scrapie of sheep, bovine spongiform encephalopathy of cattle, Creutzfeld-Jacob disease of man, whereby aberrant proteins or prion proteins are detected in tissues which can be sampled from line animals.

28 Claims, 2 Drawing Sheets

OTHER PUBLICATIONS

O'Rourke, et al. "Monoclonal Antibody F89/160.1.5 Defines a Conserved Epitope on the Ruminant Prion Protein," *Journal of Clinical Microbiology,* vol. 36, No. 6, pp. 1750–1755, Jun. 1998.

O'Rourke, et al. "Preclinical detection of $PrP^{Sc}$ in nictitating membrane lymphoid tissue of sheep," *The Veterinary Record,* pp. 489–491, May 2, 1998.

Korth et al., "Prion ($PrP^{Sc}$)–specific epitope defined by a monoclonal antibody," *Nature,* vol. 390, pp. 74–75.

Shinagawa, et al. "Immunoreactivity of a Synthetic Pentadecapeptide Corresponding to the N–Terminal Region of the Scrapie Prion Protein," *J. gen Virol.* 67, pp. 1745–1750, 1986.

Ikegami, et al. "Pre–clinical and clnical diagnosis of scrapie by detection of PrP protein in tissues of sheep," *The Veterinary Record,* pp. 271–275, Mar. 23, 1991.

Muramatsu, et al. "Detection of $PrP^{Sc}$ in sheep at the preclinical stage of scrapie and its significance for diagnosis of insidious infection," *Arch Virol,* 134, pp. 427–432, 1993.

* cited by examiner

Fig. 1A

Multiple sequence alignment of prior proteins of various origin.

Perfectly conserved: '*'       Disulfide-bond:   '$'
Well conserved:      '.'       N-Glycosylation:  '#'

```
                 ---------sign-----------
SHPRP    MVKSHIGSWILVLFVAMWSDVGLCKKRPKPGGGWNTGGSRYPGQGSPGGN     50
BTPRP    MVKSHIGSWILVLFVAMWSDVGLCKKRPKPGGGWNTGGSRYPGQGSPGGN     50
MINKPRP  MVKSHIGSWLLVLFVATWSDIGFCKKRPKPGGGWNTGGSRYPGQGSPGGN     50
GORPRP   M--ANLGYWMLVLFVATWSDLGLCKKRPKPGG-WNTGGSRYPGQGSPGGN     47
HSPRP    M--ANLGCWMLVLFVATWSDLGLCKKRPKPGG-WNTGGSRYPGQGSPGGN     47
MAPRP    M--ANLSYWLLALFVAMWTDVGLCKKRPKPGG-WNTGGSRYPGQGSPGGN     47
MMPRP    M--ANLGYWLLALFVTMWTDVGLCKKRPKPGG-WNTGGSRYPGQGSPGGN     47
RRPRP    ----------------------------------GGWNTGGSRYPGQGSPGGN   19+
                                           *  *****************

SHPRP    RYPPQGGGGWGQPHGGGWGQPHGGGWGQPHGGGWGQPHGGG--------G     92
BTPRP    RYPPQGGGGWGQPHGGGWGQPHGGGWGQPHGGGWGQPHGGGWGQPHGGGG    100
MINKPRP  RYPPQGGGGWGQPHGGGWGQPHGGGWGQPHGGGWGQPHGG---------G     92
GORPRP   RYPPQGGGGWGQPHGGGWGQPHGGGWGQPHGGGWGQPHGG---------G     88
HSPRP    RYPPQGGGGWGQPHGGGWGQPHGGGWGQPHGGGWGQPHGG---------G     88
MAPRP    RYPPQGGGTWGQPHGGGWGQPHGGGWGQPHGGGWGQPHGG---------G     88
MMPRP    RYPPQGG-TWGQPHGGGWGQPHGGSWGQPHGGSWGQPHGG---------G     87
RRPRP    RYPPQSGGTWGQPHGGGWGQPHGGGWGQPHGGGWGQPHGG---------G     60+
         *****.* .********* **********.*******.*******     *

SHPRP    WGQGG-SHSQWNKPSKPKTNMKHVAGAAAAGAVVGGLGGYMLGSAMSRPL    141
BTPRP    WGQGG-THGQWNKPSKPKTNMKHVAGAAAAGAVVGGLGGYMLGSAMSRPL    149
MINKPRP  WGQGGSHGQWGKPSKPKTNMKHVAGAAAAGAVVGGLGGYMLGSAMSRPL    142
GORPRP   WGQGGGTHSQWNKPSKPKTNMKHMAGAAAAGAVVGGLGGYMLGSAMSRPI    138
HSPRP    WGQGGGTHSQWNKPSKPKTNMKHMAGAAAAGAVVGGLGGYMLGSAMSRPI    138
MAPRP    WGQGGGTHNQWNKPSKPKTNMKHMAGAAAAGAVVGGLGGYMLGSAMSRPM    138
MMPRP    WGQGGGTHNQWNKPSKPKTNLKHVAGAAAAGAVVGGLGGYMLGSAMSRPM    137
RRPRP    WSQGGGTHNQWNKPSKPKTNLKHVAGAAAAGAVVGGLGGYMLGSAMSRPM    110+
         *.***  .*.**.********.**.*********************** .

$ #
SHPRP    IHFGNDYEDRYYRENMYRYPNQVYYRPVDRYSNQNNFVHDCVNITVKQHT    191
BTPRP    IHFGSDYEDRYYRENMHRYPNQVYYRPVDQYSNQNNFVHDCVNITVKEHT    199
MINKPRP  IHFGNDYEDRYYRENMYRYPNQVYYKPVDQYSNQNNFVHDCVNITVKQHT    192
GORPRP   IHFGSDYEDRYYRENMHRYPNQVYYRPMDQYSNQNNFVHDCVNITIKQHT    188
HSPRP    IHFGSDYEDRYYRENMHRYPNQVYYRPMDEYSNQNNFVHDCVNITIKQHT    188
MAPRP    MHFGNDWEDRYYRENMNRYPNQVYYRPVDQYNNQNNFVHDCVNITIKQHT    188
MMPRP    IHFGNDWEDRYYRENMYRYPNQVYYRPVDQYSNQNNFVHDCVNITIKQHT    187
RRPRP    LHFGNDWEDRYYRENMYRYPNQVYYRPVDQYSNQNNFVHDCVNITIKQHT    160+
         .***.*.******** ******* *.* *.************.*.**

#                  $
SHPRP    VTTTTKGENFTETDIKIMERVVEQMCITQYQRESQAYYQ--RGASVILFS    239
BTPRP    VTTTTKGENFTETDIKMMERVVEQMCITQYQRESQAYYQ--RGASVILFS    247
MINKPRP  VTTTTKGENFTETDMKIMERVVEQMCVTQYQRESEAYYQ--RGASAILFS    240
GORPRP   VTTTTKGENFTETDVKMMERVVEQMCITQYERESQAYYQ--RGSSMVLFS    236
HSPRP    VTTTTKGENFTETDVKMMERVVEQMCITQYERESQAYYQ--RGSSMVLFS    236
MAPRP    VTTTTKGENFTETDIKIMERVVEQMCTTQYQKESQAYYDGRRSSA-VLFS    237
MMPRP    VTTTTKGENFTETDVKMMERVVEQMCVTQYQKESQAYYDGRRSSSTVLFS    237
RRPRP    VTTTTKGENFTETDVKMMERVVEQMCVTQYQKESQAYYDGRRSSA-VLFS    209+
         ************* .*********** *.**.***.***   ...  ***
```

Fig. 1B

```
     ---GPI-
SHPRP      SPPVILLISFLIFLIVG   256
BTPRP      SPPVILLISFLIFLIVG   264
MINKPRP    PPPVILLISLLILLIVG   257
GORPRP     SPPVILLISFLIFLIVG   253
HSPRP      SPPVILLISFLIFLIVG   253
MAPRP      SPPVILLISFLIFLMVG   254
MMPRP      SPPVILLISFLIFLIVG   254
RRPRP      SPPVILLISFLIFLIVG   226+
           .********.**.*.**
```

Dictionary of the sequences which have been aligned
===================================================

```
[ 1]  SHPRP
DE    PROTEINSEQ OF SHPRP NT 72-839
      Size: 256 residues.
[ 2]  MINKPRP
DE    MINK TRANSL BY ALX 41-814
      Size: 257 residues.
[ 3]  GORPRP
DE    GORPRP TRANSL FROM 1-762 BY ALX
OS    GORILLA
      Size: 253 residues.
[ 4]  MAPRP
DE    MAPRP TRANSL FROM 11-733 BY ALX    AA MANLSYWLLALFVA ADDED
OS    SYRIAN GOLDEN HAMSTER
      Size: 254 residues.
[ 5]  BTPRP
DE    BOVINE PRP GENE FOR A PRION-PROTEIN.
OS    BOS TAURUS (CATTLE)
      Size: 264 residues.
[ 6]  HSPRP
DE    HOMO SAPIENS PRP GENE TRANSL FROM 50-811 BY ALX
OS    HOMO SAPIENS
      Size: 253 residues.
[ 7]  MMPRP
DE    MMPRP TRANSL FROM 107-871 BY ALX
OS    MURINE PRP
      Size: 254 residues.
[ 8]  RRPRP
DE    RAT PRION-RELATED PROTEIN (PRP) MRNA TRANSL <1? TO 678 FRAME 1
(ALX)
OS    RATTUS RATTUS (RAT)
      Size: 226 residues.
```

METHOD FOR THE DETECTION OF PRION DISEASES

CROSS REFERENCE TO RELATED APPLICATION

This application is a 371 International Application No. PCT/NL97/00166, filed on 2 Apr. 1997 designating the United States of America, the contents of which are incorporated by this reference, which itself claims priority from European Patent Office Application Serial No. 96200917.1 filed 3 Apr. 1996.

FIELD OF THE INVENTION

The invention relates to the field of prion diseases, also called spongiform encephalopathies (SEs), such as scrapie of sheep, bovine spongiform encephalopathy (BSE, mad-cow disease) of cattle, Creutzfeld-Jacob disease (CJD) and kuru of man. Prion diseases are transmissible via among others ingestion of or inoculation with prion proteins, can occur iatrogenically, but can also happen occasionally or on a hereditary basis without evidence of transmission.

BACKGROUND OF THE INVENTION

Prior diseases are a focal point of public interest, recently fuelled by the detection of unexpected cases of CJD in teenagers and in farmers, both in Great Britain, where transmisson of prion proteins from cattle to humans via meat consumption is postulated, thus indicating the transmission of BSE to humans, thereby causing CJD.

Several factors enhance public concern:
a) the nature of the causative agent, the so called prion protein, of SEs is unknown or at least controversial,
b) whatever its nature, the agent is highly resistant to procedures that eliminate other infectious agents (e.g. heating);
c) therapeutic interventions are apparently not possible, once symptoms occur;
d) SEs have an extremely long incubation period;
e) practical, sensitive and specific diagnostic methods to be used during the preclinical phase are not available.

This all adds to the general feeling of "living with a time-bomb". Not only the possible presence of prion proteins in meat and meat products poses a health threat, also the possible presence of prion proteins in blood and blood products used in transfusion, the presence in pharmaceutical products of animal origin, in cosmetics of animal origin, in sera used for cell culture, in short, in an extensive array of products of animal origin, pose possible threats to human and animal health.

Until now, confirmatory diagnosis of scrapie and also other transmissible spongiform encephalopathies depended on histological examination of the brain, collected during post-mortem examination from animals or humans with clinical signs of the disease. Deposits of an aberrant or altered protein ($PrP^{Sc}$, prion protein) can be detected in the brain of diseased animals. This protein is very insensitive to methods, such as proteinase K digestion, that otherwise denature, lyse or remove normal proteins. The aberrant protein is considered central in the pathogenesis of prion disease. Albeit not infectious in a classical microbiological way due to the absence of specific nucleic acid, the aberrant protein itself is seen as the causal agent, and when a susceptible animal obtains such an aberrant protein in its body (i.e. by ingestion, inoculation or via mutation of the gene of the normal version of the PrP protein, $Prp^C$) a chain reaction may start that ultimately will lead to a clinical manifestation of prion disease. The chain reaction entails the formation of more aberrant proteins formed out of the normal protein present in the animal's body. Normal and aberrant forms will interact in such a way that more aberrant forms are produced. Since the aberrant form is very resistant to proteolysis, deposits of the converted prion protein will be formed, especially in the brain and other parts of the central nervous system (CNS), giving rise to the spongiform encephalopathy and thus clinical manifestations of brain disease.

As SE-infected for affected animals and man lack a disease-specific immune response, identifying individuals before they develop clinical signs (which can take years) has been practically impossible so far. No biochemical, haematological, or gross pathological abnormalities are consistently associated with SEs. The diagnosis of SEs, therefore, depends on the recognition of clinical signs, electro-encephalography or magnetic resonance imaging techniques (both used only in human patients), or the more invasive method of taking brain-biopsies. The final diagnosis is made during autopsy, by histological examination of the brain. The neuro-pathological lesions, consisting of vacuolation (spongiform change) of the grey matter associated with gliosis and neuronal loss, are generally sufficiently characteristic. Further confirmation is possible by demonstrating scrapie associated fibrils (SAFs) in brain extracts, or by demonstrating the presence of its constituent protein, $PrP^{Sc}$. $PrP^{Sc}$ is associated with the disease and is an aberrant form of the host encoded prion protein (PrP), the aberrant form is induced by a conformational change. $PrP^{Sc}$ can be detected by immunological techniques such as Western blotting or immunohistochemistry. The latter technique is gradually becoming more and more accepted as a reliable diagnostic tool for clinical cases, in both the human and veterinary SE field.

The search for a practical preclinical diagnostic test has been and continues to be a main topic of research. This generally focuses on the detection of infectivity using a bio-assay, or the detection of the disease associated $PrP^{Sc}$. The bio-assay, in spite of being the most sensitive detection method, is far too cumbersome and time-consuming to ever become a practical diagnostic method: test results might become available long after the patient has passed away.

Most researchers have therefore focused on techniques to detect $PrP^{Sc}$. Although not all researchers agree with the statement that $PrP^{Sc}$ is the causative agent, most, if not all, agree that the association of the presence of $PrP^{Sc}$ and disease has been firmly established. Detection of $PrP^{Sc}$ in tissues outside the CNS would allow sampling through less invasive methods than brain biopsies, thereby brightening prospects for a practical preclinical diagnostic technique substantially. Various tissues have been used in an attempt to develop an early detection technique: blood, urine, tissue fibroblasts, and, particularly in the animal field, lymphoid tissue. A short summary of the most promising and striking ones is given here (for an extensive review see Schreuder, 1994a, 1994b).

Blood: In human SEs, there is the often disputed experimental transmission of CJD from buffy coat samples of human CJD-patients to rodents (Muaramoto et al., 1993), but there is little or no indication that blood and specifically, buffy coat contains any infectivity in animals affected naturally with scrapie, either in clinical or in preclinical stages (Fraser and Dickinson, 1978; Hadlow et al., 1982). Interesting results have recently been reported by Meiner et al. (1992) who detected $PrP^{Sc}$ in peripheral tissues, both in cultured fibroblasts and in monocytes, in a group of eight CJD patients carrying the codon 200 mutation and suffering from clinical disease. These authors used both Western blotting and immunocytochemistry techniques. Their publication, however, appears to have had no follow-up and even if these results could be confirmed, the chances for a reliable blood test seem remote, at least in the case of animal SEs and given the number of negative reports from literature (reviewed in Brown, 1995).

Urine: Only once has a claim been made that infectivity in urine was demonstrated in a case of CJD, by transmitting it to mice. The same author was, however, unable to repeat this experiment (Brown, 1995). A totally different approach was reported recently (Brugere et al., 1991). Urine from scrapie affected and control animals was tested in a voltametric method by repeated capillary micro-electrolysis, which allowed discrimination of these two groups. This approach appeared promising, but, its value in detecting preclinical stages of in particular BSE could not be confirmed.

Lymphoid tissue: Lymphoid tissue has apparently not been used in the field of diagnosing human SEs, it has, however, in the veterinary field. The already classical work by Hadlow has shown that in the lymphoid tissue of naturally infected scrapie sheep, infectivity was detectable by bio-assay as early as 10–14 months of age. This was before any infectivity in the CNS was found (Hadlow et al., 1980). Western blotting has revealed the presence of $PrP^{Sc}$ in the spleen of scrapie-infected mice (Diringer et al., 1983; Doi et al., 1988), in some cases $PrP^{Sc}$ was detected as early as 4 weeks after experimental infection. Pooled lymph nodes from these mice also contained $PrP^{Sc}$. Similarly, also using Western blotting, $PrP^{Sc}$ was detected fairly consistently in a group of naturally infected sheep showing clinical signs of scrapie, in samples from the CNS, spleen, and lymph nodes (Ikegami et al, 1991). The value of this Western blotting technique was, at least for clinical cases, confirmed by other groups. The results, however, from a group of experimentally infected sheep that were killed at 16, 18 and 21 months after inoculation but before clinical signs developed, were inconsistent and difficult to evaluate: $PrP^{Sc}$ was detected in spleen samples of only 3 out of 12 supposedly positive animals, with lymph node samples only weak or doubtful results, but no positive results were found, illustrating the insensitivity of this technique. Therefore, using Western blotting techniques in pre-clinical diagnoses of TSE give erratic and not reliable results.

The reason for these erratic results can be found in the method to prepare the $PRP^{Sc}$ protein (present in the affected tissues) and dissociate or separate it from the normal cellular isoform PrP protein that is also immunoreactive with the same antisera used for the Western blotting.

Ikegami et al. (1991) and Muramatsu et al. (1993) need to prepare the samples for Western blot analysis by various steps. They first enrich the samples by preparing tissue extracts containing fractions relatively enriched for both $PrP^{Sc}$ and PrP, after which the need to remove the PrP protein with a proteinase K treatment. This procedure entails at least 10 separate incubation and separation steps in which the absolute amount of the proteins to be detected in the sample is reduced at every step. Although this protocol works very well for the diagnosis of the clinical phase of SE's, where an abundance of $Prp^{Sc}$ is present in relation to the normal cellular isoform PrP, in the preclinical phase of TSE, the absolute amount of $PrP^{Sc}$ is so small that it usually gets lost during the preparation.

In BSE, the situation differs from that of scrapie: on the one hand, results from mice-transmission experiments using different tissues of BSE affected cattle, may indicate that distribution of the BSE agent in tissues outside the CNS is not as extensive as in the case of scrapie in sheep, on the other hand it may be that the mice used in the bio-assays are far less sensitive for BSE than for scrapie. Experimental transmission of BSE to mice only succeeded when brain material was used (Fraser et al., 1988; Fraser et al., 1990); mice inoculated with other materials, including spleen, semen, buffy coat, muscle, bone marrow and placenta remained healthy.

However, all above techniques other than bio-assays have in common that diagnosis of SEs can only be established in the clinical phase of the disease, often at autopsy only. Considering the fact that bio-assays are very slow, due to the very slow progress of the disease in the experimental animal that is used for the bio-assay as such, no methods are currently available that offer immediate diagnoses of SEs in a pre-clinical phase of the disease. Thus, although the average expert in diagnostic test development has currently a wealth of diagnostic techniques available to detect all kinds of proteins in biological samples, using monoclonal or polyclonal antisera in enzyme- or label-linked immunoassays, using techniques with or without enriching methods for the protein under study, no gold-standard is available to give guidance to the development of those diagnostic techniques that would be applicable in the case of pre-clinical diagnosis of prion disease. In other words, methods to establish sophisticated diagnostic tests are currently well known to the general expert in the field; the expert lacks, however, methods to establish the sensitivity and specificity of those sophisticated diagnostic tests due to the lack of a gold-standard.

BRIEF SUMMARY OF THE INVENTION

We have now found a reliable and fast diagnostic method for pre-clinical diagnosis of prion diseases or SE's. The invention offers a method for pre-clinical diagnosis in sheep scrapie but also for other SEs like BSE and CJD. We used scrapie in sheep as a model to study SEs. Knowledge of the group of SEs, which includes the human forms such as CJD and Kuru, has been largely obtained from studies with scrapie. Scrapie is a progressive and fatal neurological disease of sheep and goats and is considered the "archetype" of the group of SEs and the probable cause for the BSE epidemic in the United Kingdom. The control and sanitary measures taken during the outbreak of BSE in the UK were also largely based on what was known about scrapie. Taking into account the above mentioned data of Hadlow on the presence of infectivity in various peripheral tissues, we concluded that among others lymphoid tissue would be a candidate for the development of a preclinical test based on detection of $PrP^{Sc}$, but also other tissues, such as but not limited to retina, alveolar macrophases or monocytes, where PrP infectivity is found.

BRIEF DESCRIPTION OF THE DRAWINGS

FIG. 1 illustrates the multiple sequence alignment of prion proteins of various origin. Perfectly conserved amino acids are indicated by the '*' symbol; well conserved amino acids are indicated by the '.' symbol; disulfide bonds are indicated by the 'S' symbol; and N-glycosylation is indicated by the '#' symbol. The following is descriptive of the sequences disclosed in FIG. 1:

SHPRP (SEQ ID NO 1), Sheep protein sequence of SHPRP NT 72–839;

BTPRP (SEQ ID NO 2), Bovine PRP gene for a prion-protein;

MINKPRP (SEQ ID NO 3), Mink transl by ALX 41–814;
GORPRP (SEQ ID NO 4), Gorilla transl from 1–762 by ALX;
HSPRP (SEQ ID NO 5), Homo Sapiens PRP gen transl from 50–811 by ALX;
MAPRP (SEQ ID NO 6), Syrian Golden Hamster PRP gene transl. from 11–733 by ALX, AA MANLSYWLLALFVA added;
MMPRP (SEQ ID NO 7), Murine PRP transl from 107–871 by ALX; and
RRPRP (SEQ ID NO 8), Rat PRP trans<1! to 678 frame a (ALX).

DETAILED DESCRIPTION OF THE INVENTION

In our hand, immune histochemistry (IHC) using the immuno-peroxidase staining method, when used on histological sections of the brains for diagnosing clinical scrapie and BSE, proved a highly reliable and practical method for detecting $PrP^{Sc}$ (Van Keulen et al, 1995) and less-cumbersome than Western blotting. Using the same IHC-technique and the same antisera, we examined a number of lymphoid tissues in a group of naturally affected, clinically-positive scrapie sheep (n=55) (Van Keulen et al, in press, see also the experimental part). We demonstrated the presence of $PrP^{Sc}$ in the spleen, the retropharyngeal lymph node, mesenteric lymph node and the palatine tonsils, in all but one of the animals (98%). Of all examined lymph nodes, tonsils were found having the highest $PrP^{Sc}$ deposition rate that could be detected per number of follicles: in all positive cases, more than 60% of the tonsil follicles stained positive and in 95% of these cases this was even more than 80%. To assess the applicability of this method in the pre-clinical phase of scrapie, we embarked upon a study involving sequential biopsy taking of tonsils in sheep, tonsils were chosen while the experimental availability for sequential studies is guaranteed, however, using other tissues can as well be contemplated for pre-clinical diagnosis. We have detected the scrapie associated $PrP^{Sc}$ in tonsils of 10 months old sheep, which is at less than half-way the incubation period as the sheep under study are expected to develop scrapie when approximately 25 months old. In sheep that are expected to develop scrapie at a much later stage or stay healthy during their whole life span, we did not detect this $PrP^{Sc}$ protein.

With regard to scrapie, future control programs could profit from these findings. Control programs in several breeds could consist of a combination of breeding programs that make use of the established linkage between PrP genotype and increased scrapie-susceptibility or resistance, and the above described method that detects the pathognomonic presence of $PrP^{Sc}$ in tonsils of susceptible animals in the preclinical stage of the disease.

Figure 1A:
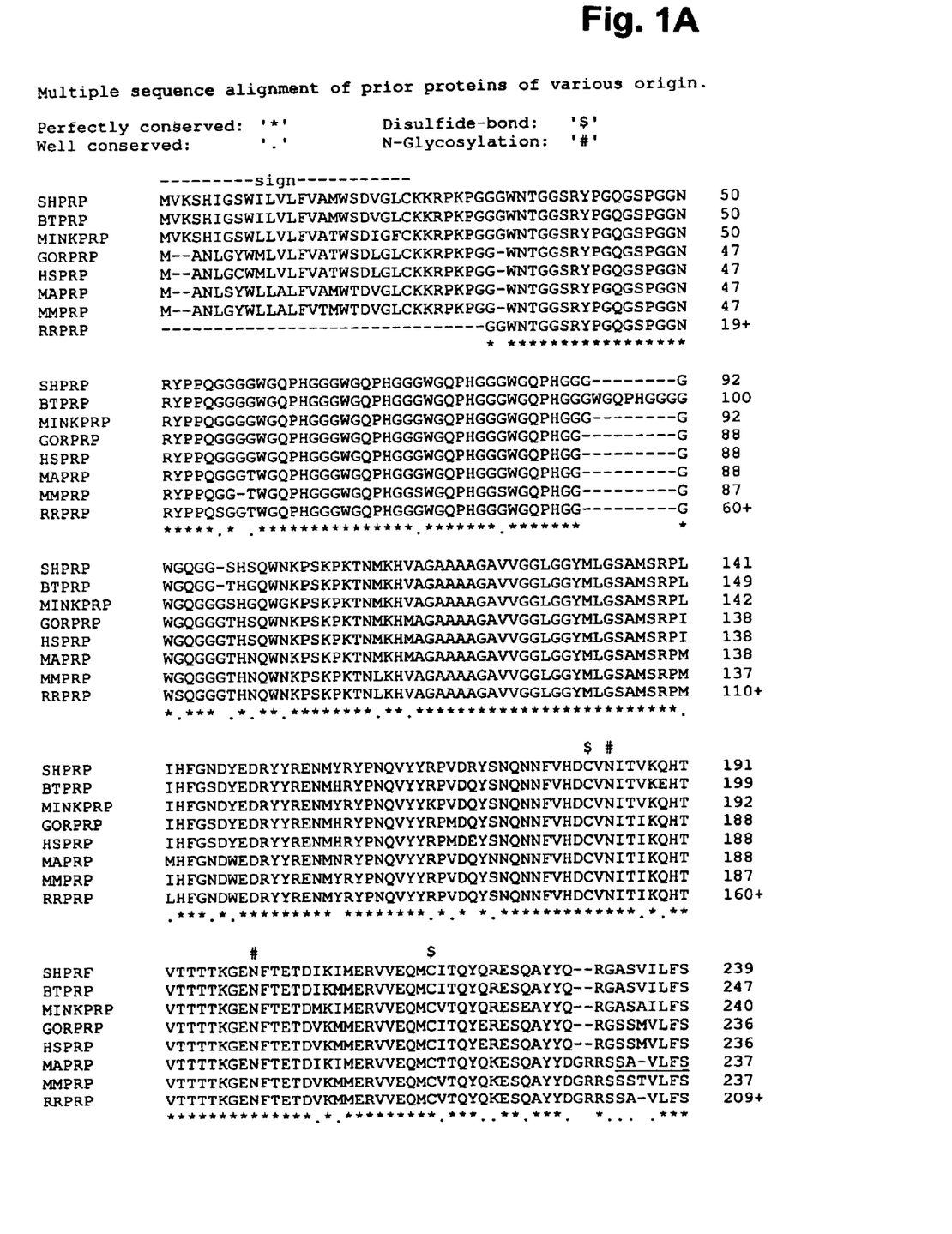
Figure 1B:
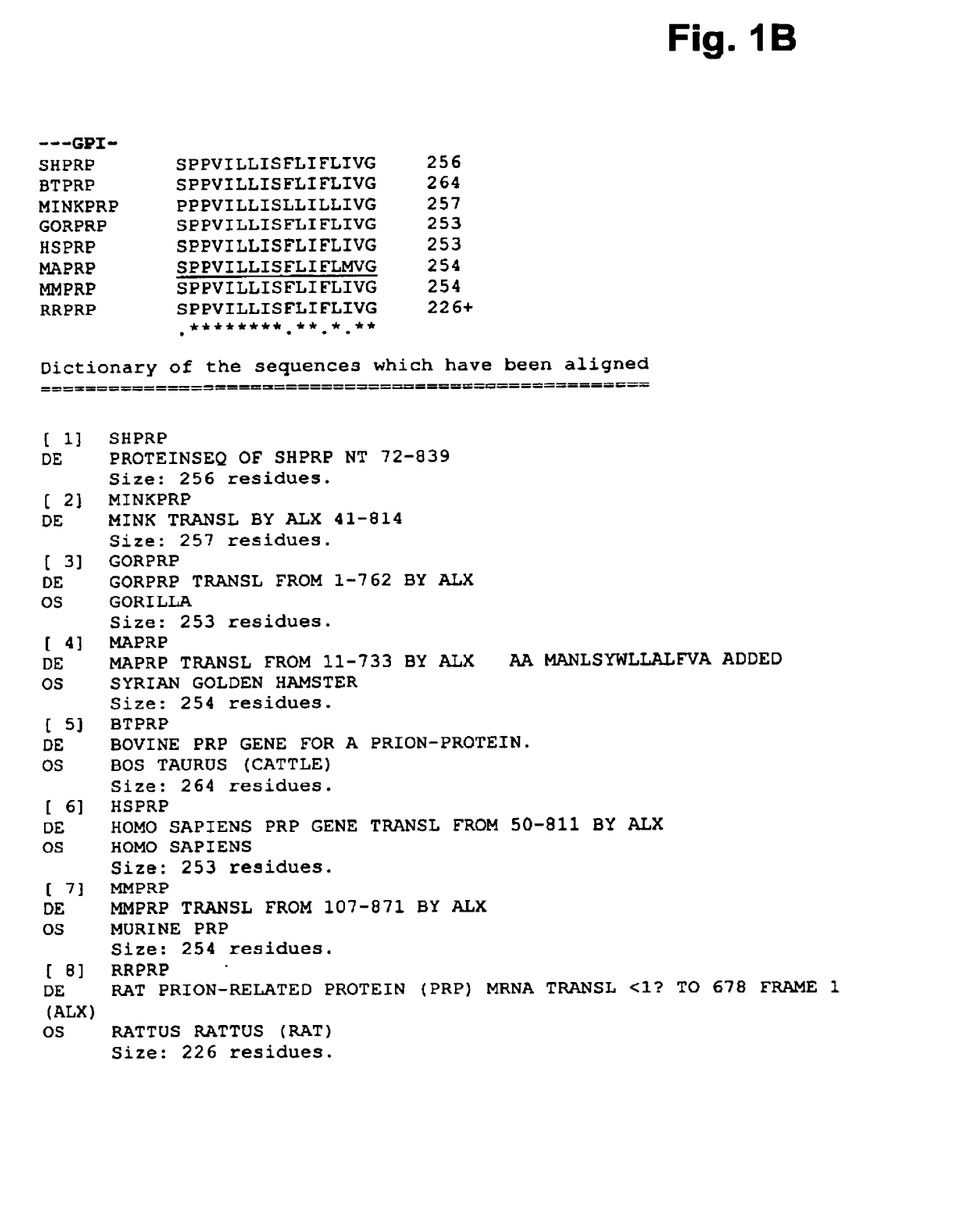

With regard to BSE, and SEs in general, changes and adjustments of the technique used can now be made to adjust to the specific circumstances and conditions of BSE, and SE, diagnosis. Those changes can be guided by specific knowledge about homologies and heterologies in the amino acid sequences of prion proteins from different species (for a selection of known sequences see FIGS. 1A and 1B). Also, guidance may found in selecting specific antisera by selecting for reactivity of selected continuous or discontinous peptide sequences of those prion proteins. First of all, the IHC-technique may be further refined for use in BSE and in peripheral lymph nodes in particular. This could require adaptations of the protocol in use for immuno-staining of brain sections. $PrP^{Sc}$ detection in lymphoid tissues has been tried only using immuno-blotting methods and in clinical cases (Mohri et al., 1992). These results were negative, indicating a detection problem with regard to sensitivity. No serious efforts have been made to detect $PrP^{Sc}$ in preclinical stages of BSE. The technique of taking tonsillar biopsies in live cattle is feasible and even easier than in sheep, as cattle can do with a light sedation (Xylazine (Rompun). The possibility of an early diagnosis in case of BSE could alleviate the need for certain draconical measures proposed today with regard to the cattle population in the UK.

Far reaching implications of our invention lie in the field of human SEs. Also here the applicability of the IHC technique in the preclinical phase can now be established. In literature, we did not find any reference to the examination of lymphoid tissues in this context. With tonsils being more readily accessible and with almost always access to a pathologic-anatomical laboratory, the above described technique, applied in human SEs, could contribute to an early diagnosis of suspected cases of SEs. This allows the possibility of detecting individuals harboring the disease at a moment early in the incubation period, at least considerably long before clinical signs appear, which in turn would allow certain therapeutic measures to be applied for specific groups at risk (at least interventions that delay the progression of the disease, such as the use of amphotericin-B).

The present invention thus provides methods for the detection of prion disease whereby aberrant proteins are detected in various tissues, such as but not limited to lymphoid or tonsillar tissue, which can be sampled from live animals, in particular from farm animals or humans or other mammals. The invention also provides methods that distinguish between aberrant and normal protein, by i.e. removing the normal protein with methods that proteolyse, hydrolyse or denature the normal protein, or by immunologically detecting the aberrant protein. Immunological detection entails any method currently known by the expert in diagnostic test development, all methods employing immunological detection with enzym- or labellinked or nonlinked antibodies, even Western blotting techniques, may now be developed into sensitive and specific techniques, due to the fact that a gold-standard for pre-clinical diagnosis of prion disease has now become available. These methods may also be developed into diagnostic tests or testkits comprising the necessary elements of any of above methods. The invention further provides use of any of above methods, tests or testkits in the diagnosis of prior disease, in disease control programs, in the selection of meat fit for consumption and in the selection of blood or blood products.

Experimental

Immunohistochemical detection of prion protein in lymphoid tissues of sheep with clinical cases of natural scrapie.

Materials and Methods

Sheep. Sixty seven sheep with nervous disorders resembling those of a scrapie infection were purchased. Fifty-five sheep were diagnosed with scrapie by histopathological and immunohistochemical examination of the brain. (Van Keulen et al., 1995) One animal suffered from both a scrapie infection and a concurrent meningo-encephalitis probably caused by *Listeria monocytogenes*. Scrapie-positive sheep originated from 30 different flocks. The group consisted of 54 females and one male ranging in age from 2 to 5 years and comprised eight different breeds and cross-breds. Twelve sheep did not show any histopathological signs of a scrapie infection nor did they display any $PrP^{Sc}$ immunostaining in the brain. Five of these sheep were diagnosed with meningo-encephalitis, one had intramyelinic edema of unknown cause, and 6 sheep showed no histopathological abnormalities. Scrapie-negative sheep were all females from 10 different flocks and two different breeds and crossbreds, ranging in age from 1 to 5 years.

Necropsy. Necropsy was performed within 36 hours after natural death or immediately after killing the animal by intravenous injection of sodium pentobarbital and exsanguination. The brain was removed from each sheep for scrapie diagnosis as described previously (van Keulen et al, 1995). Samples were taken from several lymphoid tissues including spleen, palatine tonsil, superficial cervical lymph node (prescapular lymph node), subiliac lymph node (prefemoral lymph node), medial retropharyngeal lymph node, tracheobronchila lymph node, mesenteric lymph node, and ileum.

Histological and immunohistochemical procedures. Tissue samples were immediately immersed for 24 hours in periodate-lysine-paraformaldehyde fixative (PLP) containing 2% paraformaldehyde (Merck, Darmstadt, Germany). Samples were then trimmed to a maximum thickness of 2 mm and fixed for another 24 hours in freshly prepared PLP. After fixation, tissue samples were washed in water, routinely dehydrated and embedded in paraffin. Three sections of 5 µm were cut, mounted on 3-aminoalkyltri ethoxysilane-coated glass slides (Sigma, St. Louis Mo., USA), dried for at least 48 hours at 60° C. and deparaffinized. The first section was stained with hematoxylin-eosin (HE). Second and third sections were immunostained with anti-peptide serum directed against the ovine prion protein and pre-immune serum respectively according to the following procedure; after 30 minutes immersion in 98% formic acid (Merck), sections were washed and autoclaved immersed in water for another 30 minutes at 121° C. in a pressure cooker. Endogenous peroxidase was blocked with 0.3% hydrogen peroxide in methanol (Merck). Incubation at room temperature for 1 hour with anti-peptide antiserum or pre-immune serum, diluted 1:1500 in phosphate-buffered saline (pH 7.2) containing 1% bovine serum albumin (Sigma), was followed by incubation, first with biotin-conjugate goat-anti-rabbit IgG and then with streptavidin-peroxidase for 10 and 5 minutes respectively (Dakopatts, Glostrup, Denmark). As substrate we used aminoethylcarbozole (Zymed Laboratories Inc., San Francisco Calif., USA) because its red color could easily be differentiated from the yellow-brownish ceroid/lipofuscin and hemosiderin pigment which was often present in the lymphoid tissues. Between the various steps, sections were thoroughly rinsed in phosphate-buffered saline contain 0.05% Tween-20 (Merck). Sections were counterstained with Mayer's hematoxylin for 30 seconds and mounted in Glycergel (Kakopatts). With every immunohistochemical staining, a section of the medulla oblongata of a confirmed scrapie-affected sheep was simultaneously stained for PrP to check correct immunostaining procedures.

Peptide synthesis and anti-peptide antisera. Five peptides with sequences derived from the ovine prion protein (PrP 94–105, 100–111, 126–143, 145–177, 223–234) were synthesized and used to raise anti-peptide antisera in rabbits following previously published procedures (van Keulen et al, 1995). Antisera were confirmed to be specific for PrP (both undigested and after proteinase K treatment) on western blots of partially purified prion protein from scrapie-affected sheep brain according to established procedures (Hilmert and Diringer, 1984). Pre-immune sera were collected before immunization and served as negative control sera.

The sera used have advantages which are based on a mixture of empirical, theoretical and analytical values the combination of which makes them invaluable in the diagnostic application. The preparation of the sera has been described in a publication of van Keulen et al., 1995. The immunochemical properties of these sera are partly published. The specific sera used in this example have been designed for scrapie diagnosis, however, guidance can be found in the below given indications for the development of sera that are applicable in diagnosis of the other SEs, provided one selects the sequences as corresponding to the species specific sequence of the prion protein. When needed one may select other animals than rabbits to generate the specific sera.

1: the sera have been induced with synthetic peptides with sequences based on the sequence of PrP protein.
2: the sera have been induced in rabbits.
3: the peptides sequences have such differences with the rabbit PrP sequence that they induced not only antibodies which recognized these peptides but also the authentic PrP protein.
4: the peptides used for immunization are kept short (12mers); this shortness is supposed to have a critical role in the high specificity for the scrapie forms of PrP and thus in the binding in the tissue sections even after harsh denaturing and degradative treatments.
5: the sequences used for immunization and yielding the specific scrapie PrP staining were selected from the protease K resistant domain of the $PrP^{Sc}$.
6: the sera of use in the diagnostic IHC are also well reactive in other immunochemical tests such as: Western blotting of both $PrP^{C}$ and $PrP^{Sc}$, ELISA with PrP protein, PEPSCAN with 12mer peptides with overlapping sequences of sheep PrP.
7: the peptides selected have properties (hydrophilicity, flexibility, surface occurrence) which are—when used for immunization—advantagous for eliciting antibodies with binding to the antigen on which the sequences have been based.
8: the antisera elicited show the right specificity when analyzed in PEPSCAN with 12mer peptides. The addition of a foreign dimeric glycine at either the N-terminus or the C-terminus of these peptides does not decrease the specificity of the peptides but more probably does make the immunization more effective, supposedly because it makes the peptides stand out farther away from the carrier protein and makes them more flexible on the carrier protein properties which are important determinants in antigenicity.
9: the sequences selected for peptide synthesis and immunization represent domains which have a low tendency to form secondary structure (α-helix or β-sheet) and are not part of the four regions described in the lterature a being about to forn β-sheet as synthetic peptides.

Results

Immunohistochemical testing of antipeptide antisera.

An identical and distinct immunolabelling pattern was detected with all anti-peptide antisera in the lymphoid tissues of scrapie-affected sheep. Because the five antisera were directed against different epitopes of the PrP protein, cross-reactivity of the anti-peptide antisera with another protein can be excluded. We therefore classified the immunolabelled protein as PrP. We further defined this PrP as scrapie-associated PrP ($PrP^{Sc}$), because no PrP immunoreactivity was seen in any of the lymphoid tissues of scrapie-negative sheep. Replacing the anti-peptide antisera with pre-immune sera did not result in any immunolabelling.

Localization of $PrP^{Sc}$ in the lymphoid tissues.

$PrP^{Sc}$ was located within the primary and secondary lymphoid follicles of the spleen, palatine tonsil, lymph nodes, and solitary follicles or Peyer's patches of the ileum. The PrP$^{Sc}$ immunolabelling pattern consisted of a reticular network in the center of the lymphoid follicle which varied in staining intensity. Apart from this network, fine to coarse granules of PrP$^{Sc}$ were seen in the cytoplasm of non-lymphoid cells within the follicle. Several of these cells were identified as macrophages because of the simultaneous presence of ceroid/lipofuscin pigment in their cytoplasm. No immunolabelling of the B lymphocytes in the lymphoid follicle was seen.

Occasionally, additional immunolabelling was found in specific cells and regions of the lymphoid tissues. In the spleen, individual cells in the periarterial lymphatic sheath (PALS) and the marginal zone surrounding the splenic corpuscles contained granules of PrP$^{Sc}$ sometimes combined with ceroid/lipofuscin pigment within the cytoplasm. No PrP$^{Sc}$ was seen in the red pulp of the spleen. In the palatine tonsil and ileum, branches or granules of PrP$^{Sc}$ were found interspersed between the lymphocytes of the dome area between the follicles and the crypt epithelium. In the lymph nodes, granules of PrP$^{Sc}$ were seen between the lymphocytes of the paracortex.

Distribution of PrP$^{Sc}$ in lymphoid tissues.

PrP$^{Sc}$ was detected in 54 (98%) of the 55 scrapie-affected sheep in the spleen, tonsil, retropharyngeal lymph node and mesenteric lymph node. In the tracheobronchial, prefemoral and prescapular lymph node, PrP$^{Sc}$ was seen in a slightly lower percentage of the sheep. PrP$^{Sc}$ was found in solitary lymphoid follicles or Peyer's patches of the ileum in 24 (89%) of the 27 sheep in which lymphoid tissue was present in the sections of the ileum. In only 1 of the 55 scrapie-affected sheep, Prp$^{Sc}$ could not be detected in any of the lymphoid tissues.

The percentage of lymphoid follicles that contained PrP$^{Sc}$ was estimated for the sections of the spleen, tonsil and lymph nodes. In the palatine tonsil of 98% of the scrapie-affected sheep, over 60% of the lymphoid follicles contained PrP$^{Sc}$. In the tonsils of 93% of the sheep with scrapie, the percentage of PrP$^{Sc}$-positive lymphoid follicles even exceeded 80%. In the spleen or lymph nodes. PrP$^{Sc}$ accumulation in more than 60% of the lymphoid follicles was only present in less than 30% of the sheep.

Immunohistochemical detection of prion protein in lymphoid tissues of sheep with pre-clinical cases of natural scrapie.

Material and Methods

Sheep.

We selected a group of 10 purposely bred lambs, six of them homozygous for the PrP allele with valine (V) at position 136 and glutamine (Q) at position 171. In several breeds, this PrP$^{VQ}$ allele is significantly associated with an increased susceptibility for scrapie (Belt et al, 1995). The remaining four lambs were heterozygous and possessed one PrP$^{VQ}$ allele and one PrP$^{AR}$ allele (alanine at position 136 and arginine at position 171). The PrP$^{AR}$ allele is significantly associated with increased resistance of sheep for scrapie. In a flock with natural scrapie we observed that sheep with the genotype PrP$^{VQ/VQ}$ died from scrapie at approximately 25 months of age and that the majority of the sheep with the genotype PrP$^{VQ/AR}$ were still healthy at 70 months of age. Since we expected that the PrP$^{VQ/VQ}$ sheep would almost certainly develop clinical signs of scrapie within approximately 25 months after birth and that the PrP$^{VQ/AR}$ sheep would stay healthy, we regarded these two groups of sheep as a suitable model to study changes at known stages of the incubation period. All 10 sheep were born and raised on the same farm, in an environment where scrapie has been occurring for several years. They were kept here until six months old, when they were transfered to our Institute, to a paddock where various scrapie positive animals had spent their last days.

Sampling and Testing of Tonsils of the Live Animal

Tonsil biopsies were collected under general anaesthesia, which was achieved by intravenous application of a combination of Ketalar (Ketamine-HCl) 4 mg/kg, Xylazine (Rompun) 0.05 mg/kg and Atropine 0.1 mg/kg. We used a mouth gag, a laryngoscope, and a biopsy forceps with a head of approximately 4 mm in diameter. Tonsils in sheep are not as readily accessible as in some other species, such as man, where they often protrude into the pharyngeal lumen. In sheep, they are hidden, surrounding a small cavity. It proved, however, sufficient to take a biopsy of the edge of the entrance to this cavity, the fossa tonsillaris, thereby collecting in general sufficient material (follicles) to allow examination. Some experience in the technique was obtained by collecting, just before the animals were euthanised, tonsillar biopsies from 11 sheep, among them clinically affected scrapie sheep. Histological procedures included immunostaining with specific (anti-PrP$^{Sc}$) anti-peptide-sera, as described above and in Van Keulen et al, 1995. From the 11 sheep, eight proved to be scrapie positive while three turned out negative, as was confirmed histologically and by IHC of brain tissue during post mortem examination. The tonsillar biopsies of all eight positive animals showed a positive immuno-staining in the IHC, whereas no immuno-staining could be detected in the three negative cases.

In the actual experiment, we planned to take tonsillar biopsies sequentially, at regular intervals and starting at an age of six months. For logistic reasons this was delayed. We collected biopsies from both groups for the first time at approximately 10 months after birth, when none of the sheep showed clinical signs of scrapie. The youngest sheep were nine-and-half months, the oldest sheep was 10 months and one week.

After IHC-staining we found clear, already extensive, PrP$^{Sc}$ staining in the tonsillar biopsies of all six susceptible PrP$^{VQ/VQ}$ sheep, whereas no immuno-staining was detectable in the tonsillar biopsies of any of the resistant PrP$^{VQ/AR}$ sheep. We have thus detected the scrapie associated PrP$^{Sc}$ in tonsils of 10 months old sheep, which is at less than half-way the incubation period as they are expected to develop scrapie when approximately 25 months old. In sheep that are expected to develop scrapie at a much later stage or stay healthy during their whole life span, we did not detect this PrP$^{Sc}$ protein. We conclude that IHC-staining and related methods provide the possibility for pre-clinical diagnosis in sheep scrapie as well as for other SEs like BSE and CJD.

References

Belt, P. B. G. M., I. H. Muileman, B. E. C. Schreuder, J. Bos-de Ruijter, A. L. J. Gielkens, and M. A. Smits. 1995. Identification of five allelic variants of the sheep PrP gene and their association with natural scrapie. J. Gen. Virol. 76:509–517.

Fraser, H. and A. G. Dickinson. 1978. Studies of the lymphoreticular system in the pathogenesis of scrapie: the role of spleen and thymus. J. Comp. Pathol. 88:563–573.

Hadlow, W. J., R. C. Kennedy, and R. E. Race. 1982. Natural infection of Suffolk sheep with scrapie virus. J. Infect. Dis. 146:657–664.

Hilmert, H. and H. Diringer. 1984. A rapid and efficient method to enrich SAF protein from scrapie brains of hamsters. Biosci. Rep. 4:165–170.

Ikegami, Y., M. Ito, H. Isomura, E. Momotani, K. Sasaki, Y. Muramatsu, N. Ishiguro, and M. Shinagawa. 1991. Preclinical and clinical diagnosis of scrapie by detection of PrP protein in tissues of sheep. Vet. Rec. 128:271–275.

Mohri, S., C. F. Farquhar, R. A. Somerville, M. Jeffrey, J. Foster, and J. Hope. 1992. Immunodetection of a disease specific PrP fraction in scrapie-affected sheep and BSE-affected cattle. Vet. Rec. 131:537–539.

Muramoto, T., T. Kitamoto, J. Tateishi, and I. Goto. 1993. Accumulation of abnormal prion protein in mice infected with Creutzfeldt-Jakob disease via intraperitoneal route: a sequential study. Am. J. Pathol. 143:1470–1479. van Keulen, L. J. M., B. E. C. Schreuder, R. H. Meloen, G. Mooij-Harkes, M. Poelen-van den Berg, M. E. W. Vromans, and J. Langeveld. 1995. Immunohistochemical detection and localization of prion protein in brain tissue of sheep with natural scrapie. Vet. Pathol. 32:299–308.

Brown, P. Current opinion in Hematology 2, 472–477 (1995)

Brugère H, Banissi C, Brugère-Picoux J, Chatelain J and Buvet R. Recherche d'un témoin biochimique urinaire de F'infection du mouton par la tremblante. Bull acad vet de France 1991; 64:139–45.

Diringer H, Gelderblom H, Hilmert H, Özel M, Edelblut C, and Kimberlin R H. Scrapie infectivity, fibrils and low molecular weight protein. Nature 1983; 306:476–8.

Doi S, Ito M, Shinagawa M, Sato G, Isomura H, and Goto H. Western blot detection of scrapie-associated fibril protein in tissues outside the central nervous system from preclinical scrapie-infected mice. J gen Virol 1988; 69:955–60.

Fraser H. Bruce M E, and McConnell I. Murine scrapie strains, BSE models and genetics. In: Sub-Acute spongiform Encephalopathies. Procs of a Seminar in CEC Agricultural Research Programme, Brussels, 12–14 Nov. 1990 (Bradley R, Savey M, and Marchant B A, eds.). Kluwer Academic Publishers, Dordrecht, The Netherlands 1991; 131–6.

Hadlow W J, Kennedy R C and Race R E. Natural infection of Suffolk sheep with scrapie virus, J Inf Dis 1982; 146:657–64

Hadlow W J, Kennedy R C, Race R E and Eklund C M. Virologic and histologic findings in dairy goats affected with natural scrapie. Vet Pathol 1980; 17:187–99.

Fraser H, McConnel I, Wells GAH, and Dawson M. Transmission of bovine spongiform encephalopathy to mice. Vet Rec 1988; 123:472.

Meiner Z, Halimi M, Polakiewicz R D, Prusiner S B and Gabizon R. Presence of prion protein in peropheral tissues of Libyan Jews with Creutzfeld-Jacob disease. Neurology 1992; 42, 1355–1360

Schreuder B Animal spongiform encephalopathies—an update. Part 1. Scrapie and lesser known animal spongiform encephalopathies. Vet Quart. 1994; 16, 174–181

Schreuder B Animal spongiform encephalopathies—an update. Part 2. Bovine spongiform encephalopathy. Vet Quart. 1994; 16, 182–192

Muramatsu Y, Onodera A, Horiuchi M, Ishigano N and Shinagawa M. Detection of $PrP^{Sc}$ in sheep at the preclinical stage of scrapie and its significance for diagnosis of insidious infection. Arch. Virol 134; 427–432 (1993)

---

What is claimed is:

1. A method for the immunological detection of prion disease in an animal, said method comprising:
extracting tissue from the animal; and
screening for prion disease before clinical signs of prion disease have developed, said screening comprising detecting aberrant prion proteins in the tissue extracted from the animal with an antibody induced against a peptide sequence that represents one of five domains of said aberrant prion protein, but not an epitope of a normal prion protein;
wherein said peptide sequence is selected from the group of peptide sequences consisting of: amino acid positions 94–105, 100–111, 126–143, 145–177 or 223–234 in SEQ ID NO: 1; amino acid positions 102–113, 108–119, 134–151, 153–185 or 231–242 in SEQ ID NO: 2; amino acid positions 94–106, 101–112, 127–144, 146–178 or 224–235 in SEQ ID NO: 3; amino acid positions 90–102, 97–108, 123–140, 142–174 or 220–231 in SEQ ID NO: 4, SEQ ID NO: 5, and SEQ ID NO: 6; amino acid positions 89–101, 96–107, 122–139, 141–173 or 219–230 in SEQ ID NO: 7; and amino acid positions 63–74, 69–80, 95–112, 114–146 or 192–203 in SEQ ID NO: 8.

2. The method according to claim 1, wherein the animal is mammalian.

3. The method according to claim 1, wherein the tissue is lymphoid.

4. The method according to claim 3, wherein the tissue is tonsillar.

5. The method according to claim 1, wherein the antibody distinguishes between an aberrant PrP protein and a normal PrP protein.

6. The method according to claim 5, further comprising removing normal PrP protein.

7. A diagnostic test for performing the method according to claim 1, comprising the antibody induced against the peptide sequence.

8. The diagnostic test of claim 7, further comprising enzyme- or label linked or non-linked antibodies.

9. The method according to claim 1, further comprising diagnosing prion disease in live, naturally infected animals by detecting aberrant PrP proteins.

10. A method for the immunological detection of prion disease in a subject, wherein the prion disease may be detected before clinical signs of the prion disease have developed in the subject, said method comprising:
collecting tissue from the subject;
inducing production of an antibody with specificity against at least one peptide sequence confined within a protease K resistant domain of an aberrant prion protein, but not an epitope of a normal prion protein;
screening the tissue collected from the subject for the presence of the aberrant prion protein;
said screening comprising detecting said aberrant prion protein with said antibody in the tissue;
wherein said at least one peptide sequence represents a domain having a low tendency to form secondary structure; and
wherein said antibody is reactive in an immunochemical test when analyzed with 12mer peptides having overlapping sequences with sheep PrP.

11. The method according to claim 10, wherein said at least one peptide sequence comprises a polymer having less than about 13 monomers.

12. The method according to claim 10, wherein said tissue is lymphoid tissue.

13. The method according to claim 10, wherein said tissue is tonsillar tissue.

14. The method according to claim 10, wherein said screening comprises immunohistochemical staining techniques.

15. The method according to claim 10, further comprising selecting the antibody with reactivity for a selected continuous peptide sequence confined within said protease K resistant domain of the aberrant prion protein.

16. The method according to claim 10, further comprising selecting the antibody with reactivity for a selected discontinuous peptide sequence confined within said protease K resistant domain of the aberrant prion protein.

17. A method for the immunological detection of prion disease in an animal, said method comprising:
collecting tissue from the animal;
inducing production of an antibody with specificity against at least one peptide sequence of an aberrant prion protein, but not an epitope of a normal prion protein;
screening the tissue for the presence of aberrant prion protein with said at least one antibody;
wherein the at least one peptide sequence is selected from the group of peptide sequences consisting of: amino acid positions 94–95, 100–111, 126–143, 145–177 or 223–234 in SEQ ID NO: 1; amino acid positions 102–113, 108–119, 134–151, 153–185 or 231–242 in SEQ ID NO: 2; amino acid positions 94–106, 101–112, 127–144, 146–178 or 224–235 in SEQ ID NO: 3; amino acid positions 90–102, 97–108, 123–140, 142–174 or 220–231 in SEQ ID NO: 4, SEQ ID NO: 5, and SEQ ID NO: 6; amino acid positions 89–101, 96–107, 122–139, 141–173 or 219–230 in SEQ ID NO:

7; and amino acid positions 63–74, 69–80, 95–112, 114–146 or 192–203 in SEQ ID NO: 8; and wherein the at least one antibody is also reactive in an immunochemical test when analyzed with 12mer peptides with overlapping sequences of sheep PrP.

18. The method according to claim 17, wherein said at least one peptide sequence is a synthetic peptide based on the sequence of a prion protein.

19. The method according to claim 1, wherein said screening comprises immunohistochemical staining techniques.

20. The method according to claim 17, wherein said screening comprises immunohistochemical staining techniques.

21. A method for detecting prion disease in an animal, said method comprising:

immunizing a subject other than said animal with an immunogen consisting essentially of a peptide having a sequence to induce production of an antibody having specificity for the peptide, said sequence selected from the group of sequences consisting of: amino acid positions 94–95, 100–111, 126–143, 145–177 or 223–234 in SEQ ID NO: 1; amino acid positions 102–113, 108–119, 134–151, 153–185 or 231–242 in SEQ ID NO: 2; amino acid positions 94–106, 101–112, 127–144, 146–178 or 224–235 in SEQ ID NO: 3; amino acid positions 90–102, 97–108, 123–140, 142–174 or 220–231 in SEQ ID NO: 4, SEQ ID NO: 5 and SEQ ID NO: 6; amino acid positions 89–101, 96–107, 122–139, 141–173 or 219–230 in SEQ ID NO: 7; and amino acid positions 63–74, 69–80, 95–112, 114–146 or 192–203 in SEQ ID NO: 8;

collecting the antibody from the subject;

extracting tissue from the animal; and screening for the prion disease, said screening comprising detecting prion proteins in the tissue of the animal with the antibody.

22. The method according to claim 21, wherein the sequence is amino acid positions 94–95, 100–111, 126–143, 145–177 or 223–234 in SEQ ID NO: 1.

23. A method for detecting a prion protein in a subject, said method comprising:

synthesizing a peptide having a sequence, said sequence selected from the group of sequences consisting of: amino acid positions 94–95, 100–111, 126–143, 145–177 or 223–234 in SEQ ID NO: 1; amino acid positions 102–113, 108–119, 134–151, 153–185 or 231–242 in SEQ ID NO: 2; amino acid positions 94–106, 101–112, 127–144, 146–178 or 224–235 in SEQ ID NO: 3; amino acid positions 90–102, 97–108, 123–140, 142–174 or 220–231 in SEQ ID NO: 4, SEQ ID NO: 5, and SEQ ID NO: 6; amino acid positions 89–101, 96–107, 122–139, 141–173 or 219–230 in SEQ ID NO: 7; and amino acid positions 63–74, 69–80, 95–112, 114–146 or 192–203 in SEQ ID NO: 8;

inducing production in an animal other than said subject of at least one antibody with the peptide;

extracting tissue from the subject; and screening for the prion protein in the tissue of the animal with the at least one antibody.

24. The method according to claim 10, wherein said screening is capable of detecting the prion disease in a time interval that is less than about half of an incubation time expected for the subject to develop clinical signs of the disease.

25. The method according to claim 1, wherein the peptide sequence is amino acid positions 94–105, 100–111, 126–143, 145–177 or 223–234 in SEQ ID NO: 1.

26. The method according to claim 17, wherein the peptide sequence is amino acid positions 94–95, 100–111, 126–143, 145–177 or 223–234 in SEQ ID NO: 1.

27. A method for detecting a prion protein in a subject, said method comprising:

extracting tissue from the subject; and analyzing said tissue with an antibody directed against an amino acid sequence selected from the group of amino acid sequences consisting of: amino acid positions 94–95, 100–111, 126–143, 145–177 or 223–234 in SEQ ID NO: 1; amino acid positions 102–113, 108–119, 134–151, 153–185 or 231–242 in SEQ ID NO: 2; amino acid positions 94–106, 101–112, 127–144, 146–178 or 224–235 in SEQ ID NO: 3; amino acid positions 90–102, 97–108, 123–140, 142–174 or 220–231 in SEQ ID NO: 4, SEQ ID NO: 5, and SEQ ID NO: 6; amino acid positions 89–101, 96–107, 122–139, 141–173 or 219–230 in SEQ ID NO: 7; and amino acid positions 63–74, 69–80, 95–112, 114–146 or 192–203 in SEQ ID NO: 8;

wherein the antibody is induced against an aberrant prion protein, but not an epitope of a normal prion protein.

28. The method according to claim 27, wherein the amino acid sequence is amino acid positions 94–95, 100–11, 126–143, 145–177 or 223–234 in SEQ ID NO: 1.

* * * * *

UNITED STATES PATENT AND TRADEMARK OFFICE
CERTIFICATE OF CORRECTION

PATENT NO. : 6,972,177 B1  Page 1 of 1
APPLICATION NO. : 09/155794
DATED : December 6, 2005
INVENTOR(S) : Bram Edward Cornelis Schreuder et al.

It is certified that error appears in the above-identified patent and that said Letters Patent is hereby corrected as shown below:

In the specification:

| | | |
|---|---|---|
| COLUMN 4, | LINE 53, | change "macrophases" to --macrophages-- |
| COLUMN 5, | LINE 7, | change "transl." to --transl-- |
| COLUMN 11, | LINE 10, | after "143:1470-1479." delete "van" |
| COLUMN 11, | LINE 11, | at the beginning of the line insert --van-- |

Signed and Sealed this

Twenty-first Day of July, 2009

JOHN DOLL
*Acting Director of the United States Patent and Trademark Office*

SEQUENCE LISTING

<160> NUMBER OF SEQ ID NOS: 8

<210> SEQ ID NO 1
<211> LENGTH: 256
<212> TYPE: PRT
<213> ORGANISM: Ovis aries

<400> SEQUENCE: 1

```
Met Val Lys Ser His Ile Gly Ser Trp Ile Leu Val Leu Phe Val Ala
 1               5                  10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Gly Trp Gly Gln Gly
                85                  90                  95

Gly Ser His Ser Gln Trp Asn Lys Pro Ser Lys Pro Lys Thr Asn Met
            100                 105                 110

Lys His Val Ala Gly Ala Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160
```

```
Pro Asn Gln Val Tyr Tyr Arg Pro Val Asp Arg Tyr Ser Asn Gln Asn
            165                 170                 175

Asn Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Ile
            195                 200                 205

Met Glu Arg Val Val Glu Gln Met Cys Ile Thr Gln Tyr Gln Arg Glu
210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
            245                 250                 255

<210> SEQ ID NO 2
<211> LENGTH: 264
<212> TYPE: PRT
<213> ORGANISM: Bos taurus

<400> SEQUENCE: 2

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Pro His
            85                  90                  95

Gly Gly Gly Gly Trp Gly Gln Gly Gly Thr His Gly Gln Trp Asn Lys
            100                 105                 110

Pro Ser Lys Pro Lys Thr Asn Met Lys His Val Ala Gly Ala Ala Ala
            115                 120                 125

Ala Gly Ala Val Val Gly Gly Leu Gly Gly Tyr Met Leu Gly Ser Ala
130                 135                 140

Met Ser Arg Pro Leu Ile His Phe Gly Ser Asp Tyr Glu Asp Arg Tyr
145                 150                 155                 160

Tyr Arg Glu Asn Met Tyr Arg Tyr Pro Asn Gln Val Tyr Tyr Arg Pro
            165                 170                 175

Val Asp Gln Tyr Ser Asn Gln Asn Asn Phe Val His Asp Cys Val Asn
            180                 185                 190

Ile Thr Val Lys Glu His Thr Val Thr Thr Thr Thr Lys Gly Glu Asn
            195                 200                 205

Phe Thr Glu Thr Asp Ile Lys Met Met Glu Arg Val Val Glu Gln Met
210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Pro Val Ile Leu Leu Ile Ser
            245                 250                 255

Phe Leu Ile Phe Leu Ile Val Gly
            260
```

-continued

<210> SEQ ID NO 3
<211> LENGTH: 257
<212> TYPE: PRT
<213> ORGANISM: Mustela sp.

<400> SEQUENCE: 3

```
Met Val Lys Ser His Ile Gly Ser Trp Leu Leu Val Leu Phe Val Ala
 1               5                  10                  15

Thr Trp Ser Asp Val Gly Phe Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Gly
                85                  90                  95

Gly Gly Ser His Ser Gln Trp Gly Lys Pro Ser Lys Pro Lys Thr Asn
            100                 105                 110

Met Lys His Val Ala Gly Ala Ala Ala Gly Ala Val Val Gly Gly
        115                 120                 125

Leu Gly Gly Tyr Met Leu Gly Ser Ala Met Ser Arg Pro Leu Ile His
    130                 135                 140

Phe Gly Asn Asp Tyr Glu Asp Arg Tyr Tyr Arg Glu Asn Met Tyr Arg
145                 150                 155                 160

Tyr Pro Asn Gln Val Tyr Tyr Arg Pro Val Asp Gln Tyr Ser Asn Gln
                165                 170                 175

Asn Asn Phe Val His Asp Cys Val Asn Ile Thr Val Lys Gln His Thr
            180                 185                 190

Val Thr Thr Thr Thr Lys Gly Glu Asn Phe Thr Glu Thr Asp Met Lys
        195                 200                 205

Ile Met Glu Arg Val Val Glu Gln Met Cys Val Thr Gln Tyr Gln Arg
    210                 215                 220

Glu Ser Glu Ala Tyr Tyr Gln Arg Gly Ala Ser Ala Ile Leu Phe Ser
225                 230                 235                 240

Pro Pro Pro Val Ile Leu Leu Ile Ser Leu Leu Ile Leu Leu Ile Val
                245                 250                 255

Gly
```

<210> SEQ ID NO 4
<211> LENGTH: 253
<212> TYPE: PRT
<213> ORGANISM: Gorilla gorilla

<400> SEQUENCE: 4

```
Met Ala Asn Leu Gly Tyr Trp Met Leu Val Leu Phe Val Ala Thr Trp
 1               5                  10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Trp Gly Gln Pro His Gly Gly Gly
65                  70                  75                  80
```

-continued

```
Trp Gly Gln Pro His Gly Gly Trp Gly Gln Gly Gly Thr His
             85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
            115                 120                 125

Met Leu Gly Ser Ala Met Ser Arg Pro Ile Ile His Phe Gly Ser Asp
130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250
```

<210> SEQ ID NO 5
<211> LENGTH: 253
<212> TYPE: PRT
<213> ORGANISM: Homo sapiens

<400> SEQUENCE: 5

```
Met Ala Asn Leu Gly Cys Trp Met Leu Val Leu Phe Val Ala Thr Trp
  1               5                  10                  15

Ser Asp Leu Gly Leu Cys Lys Lys Arg Pro Lys Pro Gly Gly Trp Asn
             20                  25                  30

Thr Gly Gly Ser Arg Tyr Pro Gly Gln Gly Ser Pro Gly Gly Asn Arg
         35                  40                  45

Tyr Pro Pro Gln Gly Gly Gly Trp Gly Gln Pro His Gly Gly Gly
 50                  55                  60

Trp Gly Gln Pro His Gly Gly Trp Gly Gln Pro His Gly Gly Gly
 65                  70                  75                  80

Trp Gly Gln Pro His Gly Gly Gly Trp Gly Gln Gly Gly Thr His
             85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
            115                 120                 125

Met Leu Gly Ser Ala Met Ser Arg Pro Ile Ile His Phe Gly Ser Asp
130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205
```

```
Val Val Glu Gln Met Cys Ile Thr Gln Tyr Glu Arg Glu Ser Gln Ala
        210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 6
<211> LENGTH: 254
<212> TYPE: PRT
<213> ORGANISM: Syrian Golden Hamster

<400> SEQUENCE: 6

Met Ala Asn Leu Ser Tyr Trp Leu Leu Ala Leu Phe Val Ala Met Trp
 1               5                  10                  15

Thr Asp Val Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Gly Thr Trp Gly Gln Pro His Gly Gly Gly
        50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Asn Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Met Met His Phe Gly Asn Asp
    130                 135                 140

Trp Glu Asp Arg Tyr Tyr Arg Glu Asn Met Asn Arg Tyr Pro Asn Gln
145                 150                 155                 160

Val Tyr Tyr Arg Pro Val Asp Gln Tyr Asn Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Ile Lys Ile Met Glu Arg
        195                 200                 205

Val Val Glu Gln Met Cys Thr Thr Gln Tyr Gln Lys Glu Ser Gln Ala
    210                 215                 220

Tyr Tyr Asp Gly Arg Arg Ser Ser Ala Val Leu Phe Ser Ser Pro Pro
225                 230                 235                 240

Val Ile Leu Leu Ile Ser Phe Leu Ile Phe Leu Met Val Gly
                245                 250

<210> SEQ ID NO 7
<211> LENGTH: 254
<212> TYPE: PRT
<213> ORGANISM: Murinae gen. sp.

<400> SEQUENCE: 7

Met Ala Asn Leu Gly Tyr Trp Leu Leu Ala Leu Phe Val Thr Met Trp
 1               5                  10                  15

Thr Asp Val Gly Leu Cys Lys Lys Arg Pro Lys Pro Gly Gly Trp Asn
                20                  25                  30
```

-continued

```
Thr Gly Gly Ser Arg Tyr Pro Gly Gln Gly Ser Pro Gly Gly Asn Arg
         35                  40                  45

Tyr Pro Pro Gln Gly Gly Thr Trp Gly Gln Pro His Gly Gly Gly Trp
 50                  55                  60

Gly Gln Pro His Gly Gly Ser Trp Gly Gln Pro His Gly Gly Ser Trp
 65                  70                  75                  80

Gly Gln Pro His Gly Gly Trp Gly Gln Gly Gly Thr His Asn
                 85                  90                  95

Gln Trp Asn Lys Pro Ser Lys Pro Lys Thr Asn Leu Lys His Val Ala
                100                 105                 110

Gly Ala Ala Ala Gly Ala Val Val Gly Leu Gly Gly Tyr Met
        115                 120                 125

Leu Gly Ser Ala Met Ser Arg Pro Met Ile His Phe Gly Asn Asp Trp
130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
                180                 185                 190

Lys Gly Glu Asn Phe Thr Glu Thr Asp Val Lys Met Met Glu Arg Val
                195                 200                 205

Val Glu Gln Met Cys Val Thr Gln Tyr Gln Lys Glu Ser Gln Ala Tyr
        210                 215                 220

Tyr Asp Gly Arg Arg Ser Ser Thr Val Leu Phe Ser Ser Pro Pro
225                 230                 235                 240

Val Ile Leu Leu Ile Ser Phe Leu Ile Phe Leu Ile Val Gly
                245                 250
```

<210> SEQ ID NO 8
<211> LENGTH: 226
<212> TYPE: PRT
<213> ORGANISM: Rattus rattus

<400> SEQUENCE: 8

```
Gly Gly Trp Asn Thr Gly Gly Ser Arg Tyr Pro Gly Gln Gly Ser Pro
 1               5                  10                  15

Gly Gly Asn Arg Tyr Pro Pro Gln Ser Gly Gly Thr Trp Gly Gln Pro
             20                  25                  30

His Gly Gly Gly Trp Gly Gln Pro His Gly Gly Trp Gly Gln Pro
         35                  40                  45

His Gly Gly Gly Trp Gly Gln Pro His Gly Gly Trp Ser Gln Gly
     50                  55                  60

Gly Gly Thr His Asn Gln Trp Asn Lys Pro Ser Lys Pro Lys Thr Asn
 65                  70                  75                  80

Leu Lys His Val Ala Gly Ala Ala Ala Gly Ala Val Val Gly Gly
                 85                  90                  95

Leu Gly Gly Tyr Met Leu Gly Ser Ala Met Ser Arg Pro Met Leu His
                100                 105                 110

Phe Gly Asn Asp Trp Glu Asp Arg Tyr Tyr Arg Glu Asn Met Tyr Arg
                115                 120                 125

Tyr Pro Asn Gln Val Tyr Tyr Arg Pro Val Asp Gln Tyr Ser Asn Gln
                130                 135                 140

Asn Asn Phe Val His Asp Cys Val Asn Ile Thr Ile Lys Gln His Thr
145                 150                 155                 160
```

-continued

```
Val Thr Thr Thr Thr Lys Gly Glu Asn Phe Thr Glu Thr Asp Val Lys
                165             170             175

Met Met Glu Arg Val Val Glu Gln Met Cys Val Thr Gln Tyr Gln Lys
            180             185             190

Glu Ser Gln Ala Tyr Tyr Asp Gly Arg Arg Ser Ser Ala Val Leu Phe
        195             200             205

Ser Ser Pro Pro Val Ile Leu Leu Ile Ser Phe Leu Ile Phe Leu Ile
    210             215             220

Val Gly
225
```